United States Patent [19]

Putz

[11] Patent Number: 5,044,368
[45] Date of Patent: Sep. 3, 1991

[54] DIAGNOSTIC ELECTRODE FOR USE WITH MAGNETIC RESONANCE IMAGING

[75] Inventor: David A. Putz, Racine, Wis.

[73] Assignee: Ad-Tech Medical Instrument Corporation, Racine, Wis.

[21] Appl. No.: 512,862

[22] Filed: Apr. 23, 1990

[51] Int. Cl.$^5$ ............................................... A61B 5/04
[52] U.S. Cl. .................................................... 128/642
[58] Field of Search ............... 128/639, 642, 784, 798; 604/280

[56] References Cited

U.S. PATENT DOCUMENTS 4,245,645 1/1981 Arseneault et al. ................. 128/642
4,735,208 4/1988 Wyler et al. ......................... 128/642
4,796,637 1/1989 Mascuch et al. ............... 604/280 X

FOREIGN PATENT DOCUMENTS 2454640 12/1980 France ................................ 128/642
0175837 7/1989 Japan .................................. 128/639

OTHER PUBLICATIONS

Stuyck et al, "A Suitable Type of Wire . . . ", Ellectromyogr. Clin Neur., 1975, No. 3, 15, p. 291.

Primary Examiner—Lee S. Cohen
Attorney, Agent, or Firm—Peter N. Jansson, Ltd.

[57] ABSTRACT

An improved intracranial diagnostic electrode for use with magnetic resonance imaging techniques includes an electrode body and at least one metallic contact supported by the body. An electrical lead wire is attached to the contact for connecting the contact to a diagnostic instrument. At least the metallic contact is made of an alloy which includes nickel and chromium and is substantially devoid of iron. The electrode thereby provides substantially clear images of the location of each metallic contact when the electrode is used in conjunction with magnetic resonance imaging techniques. The electrode may also include radiopaque elements or markers to adapt the electrode for use with x-ray as well as magnetic resonance imaging techniques. Several embodiments are disclosed.

6 Claims, 1 Drawing Sheet

DIAGNOSTIC ELECTRODE FOR USE WITH MAGNETIC RESONANCE IMAGING

Field of the Invention

This invention is related generally to sensing devices for use in defining epileptogenic foci and, more particularly, to diagnostic electrodes for use with magnetic resonance image techniques employed to help define such foci.

BACKGROUND OF THE INVENTION

Surgical removal of epileptogenic brain tissue is indicated for treatment of many medically refractory focal seizure disorders, epilepsy being by far the most common. One of the important factors in providing good results from such surgery is the degree of accuracy in identifying epileptogenic foci. This involves sensing of cortical electrical activity using various types of diagnostic electrodes and, especially, the electrical contacts which form a part of such electrodes.

In recent years many epilepsy centers have used intracranial recording techniques to better define regions of cortical epileptogenicity. Broadly speaking, intracranial sensing techniques have used two different kinds of electrodes for engagement with brain tissue. These different kinds include depth electrodes which are long, thin devices inserted into the brain and having one or more electrical contacts arranged along their length. Another kind of electrode is the subdural type which is placed between the dura and the brain and in contact with the brain, but not within the brain. Such subdural electrodes are known either as strip or grid electrodes, depending primarily on whether they have one or more rows, respectively, of electrical contacts.

These kinds of electrodes each have an electrode body which is formed of a dielectric material. Depth electrodes typically have a thin, tubular body with ring-like contacts sleeved over and spaced along the body. These contacts touch brain tissue to sense electrical signals present in the tissue. A separate lead wire connect to each of the contacts and extends inside the tubular body in a direction away from the distal end of the depth electrode, i.e., that end which is inserted into the brain.

Subdural strip and grid electrodes each have at least one metallic contact and preferably a plurality of such contacts supported by the body in a spaced relationship one to the other. The electrical contacts and the lead wire extending from each are held between two thin, flat layers of dielectric material which are joined as one in the assembly process. One of these layers has a hole through it for each contact in the electrode. Such holes permit the contact to touch brain tissue and, like the contacts of the depth electrodes, directly sense electrical signals therefrom.

Depth electrodes are shown in U.S. Pat. No. 4,245,645 (Arseneault et al.) while subdural electrodes are shown in U.S. Pat. No. 4,735,208 (Wyler et al.).

Knowing the precise locations of the contacts of such electrodes is essential for accurate interpretation of the electrical signals which they sense. Electrical signals picked up by intracranial contacts can be accurately associated with a specific location in the brain only to the extent that the precise locations of the contacts vis-a-vis the brain are known. Contact location is by the use of x-ray, computerized axial tomography (CAT) and/or, more recently, magnetic resonance imaging (MRI) techniques. Since surgical removal of diseased brain is an intended subsequent course of action, accuracy in determining the location of diseased brain is of paramount importance. The substantial risks involved with removal of brain tissue are apparent.

Heretofore, such electrodes have used contacts and lead wires which are made of stainless steel or of a precious metal. With the advent of MRI techniques, on a commercial level in about 1984 in the United States, certain difficulties have been encountered in using stainless steel for such contacts and lead wires. These difficulties have persisted and until the advent of the inventive electrode, have defied solution.

Specifically, electrodes which use contacts and lead wires of stainless steel (or other biocompatible ironbearing materials) produce what is known as an artifact. An artifact is an area of very significant image blurring which extends from and beyond the edge of the electrical contact and the lead wire and prevents the treating physician from understanding the precise location of the contact. Since the identification of epileptogenic foci is extremely important in successfully treating focal seizure disorders, the presence of the artifact or image blurring makes such treatment unnecessarily difficult. While precious metals do not present such difficulties, the cost of using such metals (including platinum) is prohibitive.

Yet another difficulty relates to the fact that the electrical contacts on depth electrodes are sleeve-like and hollow and cylindrical in shape. When such contacts are made of stainless steel or other iron-bearing materials, the use of MRI equipment may cause stray magnetic flux to circulate in the contact and the result is an even more significant location-obscuring artifact.

Still another disadvantage which arises from the use of stainless steel or other iron-bearing contact and wire materials is that they exhibit magnetic properties. As a result, electrodes which employ such contacts and lead wires tend to move from the intracranial location or at least are urged toward movement. This characteristic is particularly disadvantageous in the case of subdural electrodes. Such subdural electrodes, unlike depth electrodes which are lodged in tissue, are somewhat more free to move in their positions between the dura and the brain tissue.

In addition, diagnostic electrodes of the kinds described above may also be used with x-ray diagnostic techniques. With such techniques, it is equally important for the treating physician to be able ascertain the precise locations of the contacts of such electrodes. Checks on the precise location of the contacts of such electrodes by the use of x-rays has been difficult primarily because of the nature of the electrical contacts. This is particularly the case with subdural strip and grid electrodes where the contacts are so thin and delicate that they can not be seen or seen readily at desired x-ray powers.

There is a significant and long-felt need for an improved diagnostic electrode which permits precise location of the intracranial positions of the electrical contacts when the electrodes are used with MRI diagnostic techniques. It would be additionally advantageous for such an electrode to be constructed so that the location of its contacts can be accurately determined when using x-ray diagnostic techniques.

OBJECTS OF THE INVENTION

It is an object of this invention to provide an improved diagnostic electrode which overcomes some of the problems and shortcomings of the prior art.

Another object of this invention is to provide an improved diagnostic electrode which is compatible with MRI techniques.

Another object of this invention is to provide an improved diagnostic electrode wherein the electrical contacts are substantially devoid of iron-bearing material.

Another object of this invention is to provide an improved diagnostic electrode wherein the electrical contacts are made of a nickel-chromium alloy.

Another object of this invention is to provide an improved electrode which may incorporate a radiopaque element, the position of which is readily discernible using x-ray diagnostic techniques.

These and other important objects will be apparent from the descriptions of this invention which follow.

SUMMARY OF THE INVENTION

An improved diagnostic electrode for use with magnetic resonance imaging techniques includes an electrode body and at least one metallic contact supported by the body. An electrical lead wire is attached to the contact for connecting the contact to a diagnostic instrument. At least the metallic contact is made of an alloy which includes nickel and chromium and is substantially devoid of iron. The electrode thereby provides substantially clear images of the location of each metallic contact when the electrode is used in conjunction with magnetic resonance imaging techniques.

In one preferred embodiment, the electrode is constructed as a depth electrode having a thin elongate electrode body made of a tubular dielectric material. Several sleeve-like metallic contacts are arranged in spaced locations along the body. In a highly preferred embodiment, both the contacts and the body are circular in cross-sectional shape.

A lead wire is attached to each contact and extends through a small aperture in the wall of the body and from thence along the body interior passage in a direction away from the distal end of the electrode. Each lead wire is coated with an insulating material and the group of wires is brought to the exterior of the electrode body for connection to a diagnostic instrument. At least the metallic contact is made of a nickel-chromium alloy and a highly preferred alloy is approximately 80% nickel and 20% chromium.

In another preferred embodiment, the electrode is constructed as a subdural strip electrode which has at least one, and preferably a plurality of thin, disc shaped metallic contacts arranged in spaced locations along the body. Each contact has an electrical lead wire attached to it for connecting the contact to a diagnostic instrument. The lead wires are coated with a insulating material and both the contacts and their associated wires are confined between two thin, flat flexible strips of material. One of these strips has openings formed in it at spaced locations to permit the metallic contact to touch the brain tissue and sense electrical signals from such tissue.

In still another embodiment, the electrode is constructed as a subdural grid electrode which has at least two rows of metallic contacts, each contact being spaced from one another. When so arranged, these contacts define an array. Construction of the grid electrode is similar to that of the strip electrode in that the contacts and their associated wires are confined between thin, flat flexible strips of dielectric material. One strip has openings formed in it at the location of each contact so that the bare contact may touch brain tissue and sense electrical signals from such tissue.

In all of the embodiments described above, at least each metallic contact is made of a nickel-chromium alloy. Preferred alloys are substantially devoid of iron but may have trace amounts of maganese and/or silicon and other constituents as may be required to cause proper mixture of the nickel and chromium in the molten state.

The embodiments described above are highly suitable for use with MRI diagnostic techniques in that the location of the contacts is readily discernible. That is, the image created by the contacts will be substantially devoid of artifact. Further, neither the position nor the image of such contacts will be affected by stray magnetic flux.

However, a highly preferred embodiment of the electrode is also usable with x-ray diagnostic techniques. Therefore, such electrode will also include an integrated radiopaque element. When the electrode is constructed as a depth electrode, the electrode body is preferably formed of a dielectric plastic material filled with barium sulfate, thus making the body opaque to x-rays.

When the electrode is constructed as a subdural strip electrode, a radiopaque dielectric marker embodied as a thin annular ring or thin disc is placed adjacent that contact at the distal end of the electrode or adjacent each contact of the electrode. In addition, the lead wires which protrude from the proximal end of the electrode are encased in a length of radiopaque dielectric sheathing. The sheathing and marker enable the treating physician to discern the extermities of the electrode and, therefore, the location of intermediate contacts with a high degree of precision.

The construction of the subdural grid electrode is similar to that of the strip electrode. One difference is that radiopaque annular ring markers or discs are placed adjacent those contacts at the four corners of the electrode or adjacent all contacts. Such markers, together with radiopaque sheathing of the exiting lead wires, permits location of all contacts.

DETAILED DESCRIPTIONS OF PREFERRED EMBODIMENTS

The figures illustrate several preferred embodiments of the inventive electrode 10.

Figure 1:
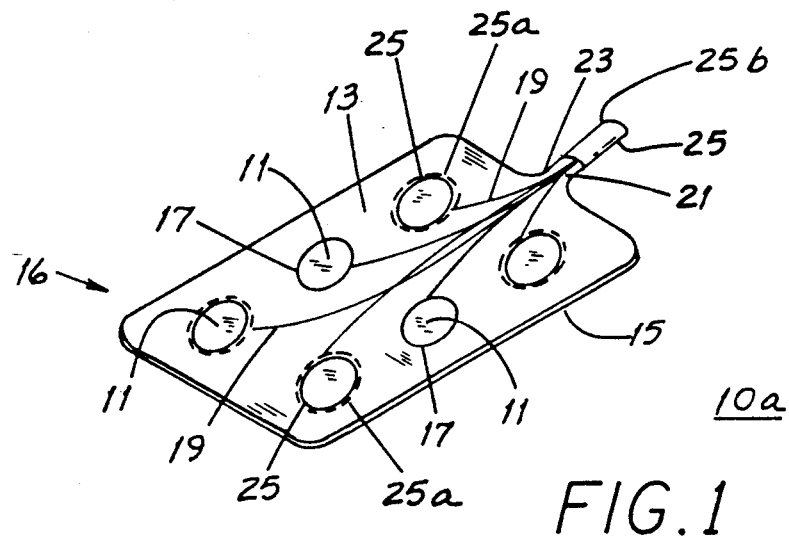
FIG. 1 is a bottom perspective view, greatly enlarged, of an electrode of the subdural grid type.

Referring to FIG. 1, the first embodiment 10a of the inventive electrode 10 (of the subdural grid type) includes an array of electrode discs 11 interposed between a lower dielectric layer 13 and an upper dielectric layer 15 which form the electrode body 16. The lower layer 13, that which is in contact with the brain when the electrode 10a is inserted, has a plurality of regularly spaced openings 17 through it for exposing an electrode disc 11 at each opening 17. Each disc 11 is connected to a separate electrical lead wire 19, such wires 19 being covered with an insulating coating and brought to a common exit point 21 at the proximal end 23 of the electrode 10a. This facilitates connection of each disc or contact 11 of an electrode 10a to a diagnostic instrument. In the illustrated embodiment 10a, the contacts 11 are thin, flat, disc shaped and have a diameter slightly greater than that of the related opening 17. The contacts 11 are thereby maintained in a position between the upper layer 15 and the lower layer 13.

Figure 2:
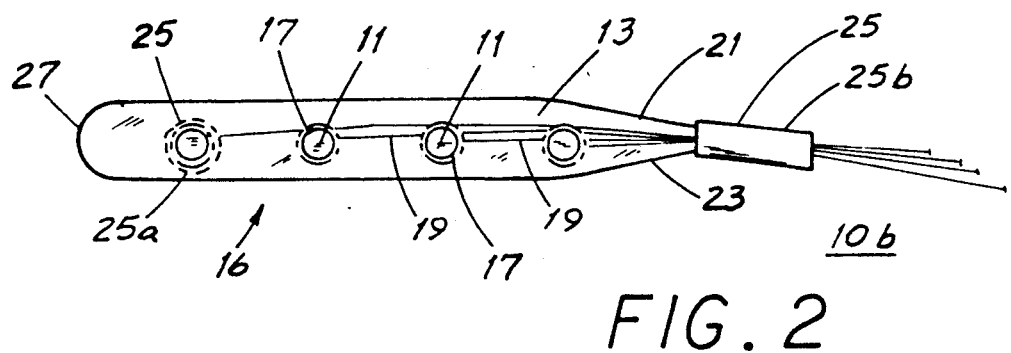
FIG. 2 is a bottom plan view, greatly enlarged, of an electrode of the subdural strip type.

Referring next to FIG. 2, the second embodiment 10b of the electrode 10 (of the subdural strip type) has at least one and preferably a plurality of electrode contacts 11 interposed and confined between a lower dielectric layer 13 and an upper dielectric layer (not shown) which form the electrode body 16. Like the layer 13 of FIG. 1, the lower dielectric layer 13 has a plurality of openings 17 formed in it for exposing an electrode contact 11 at each opening 17. Similarly, each contact 11 is connected to a separate, insulated electrical lead wire 19 and brought to a common exit point 21 adjacent the proximal end 23 of the electrode 10b. As in the embodiment of FIG. 1, the contacts 11 of the electrode 10b in FIG. 2 are thin, flat, disc shaped and have a diameter slightly in excess of that of the related opening 17 through which they are exposed to contact brain tissue.

Figure 3:
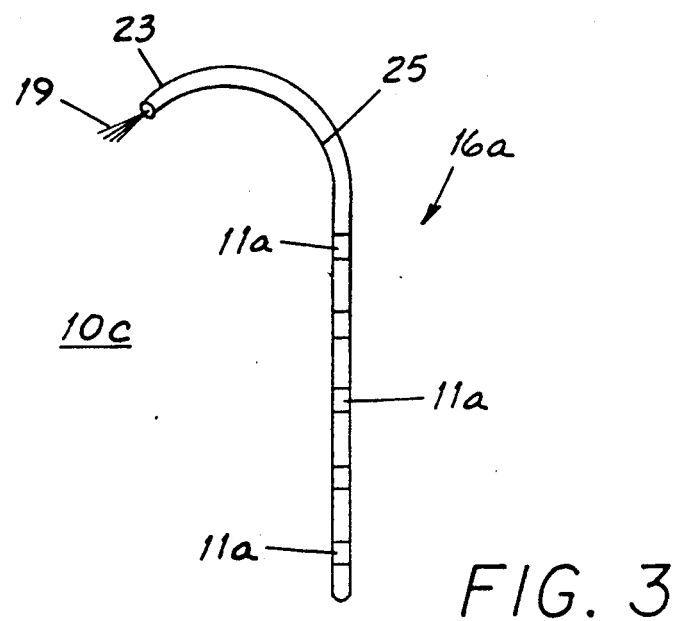
FIG. 3 is a side elevation view, greatly enlarged, of an electrode of the depth type.

Referring next to FIG. 3, the third embodiment 10c of the improved electrode 10 (of the depth type) includes a thin, elongate body 16a formed of a tubular dielectric material. At least one and preferably several electrical contacts 11a are mounted on the body 16a in a regularly spaced relationship from one another. Each such contact 11a has an electrical lead wire 19 attached thereto, the wire 19 being inserted through a small hole (not shown) in the side wall of the body 16a. When the electrode 10c is finally assembled, this hole is covered by the contact 11a. All such lead wires 19 are coated with an insulating material and are brought to the proximal end 23 of the electrode 10c for connection to a diagnostic instrument.

In the embodiments of FIG. 1-3, at least the metallic contacts 11, 11a and preferably also the associated lead wires 19 are made of an alloy which includes nickel and chromium and which is substantially devoid of iron and is essentially non-magnetic. A highly preferred alloy includes about 0.08-0.25% carbon, about 0.6-1.0% manganese, about 0.45% silicon, about 1.0% iron, about 19-20% chromium and the remainder, about 79-80% nickel.

It is to be appreciated that because of the low mass of the electrical contacts 11 used in the first and second embodiments 10a, 10b of the electrode 10, artifacts and image "fuzziness" or blurring are less of a problem than in the electrode 10 of the third embodiment 10c when iron-bearing stainless steel is used. However, image quality and the resulting ability to determine accurate contact location are improved in all embodiments 10a, 10b, 10c when contacts 11, 11a and wire 19 of a nickel-chromium alloy are used.

In the above described embodiments 10a, 10b, 10c, the electrode 10 is highly suitable for use with MRI techniques. This is so since the substantial absence of iron results in an image of each contact 11, 11a which is quite sharp and substantially devoid of artifact or fuzziness and blurring at the contact edges. However, it may also be desirable to have an electrode 10 which is not only highly compatible with MRI diagnostic techniques but which can also be used successfully with x-ray techniques.

Accordingly, each electrode embodiment 10a, 10b, 10c may also include one or more radiopaque elements 25 integrated into it. The use of such radiopaque elements 25 per se is known. Referring to FIG. 1, adequate resolution of the location of the contacts 11 can be accomplished using x-ray if the treating physician can ascertain the location of the contact 11 at each corner of the electrode 10a and can also ascertain the location of the proximal end 23 of the electrode 10a. To that end, a radiopaque element 25 embodied as a thin annular ring or thin disc 25a may be located concentric with and adjacent the contact 11 at each of the four corners or adjacent all contacts 11. Each element 25 is held in place between the contact 11 and the upper layer 15. Additionally, a length of radiopaque dielectric sheathing 25b may be installed at the proximal end 23 of the electrode 10a.

In the embodiment 10b of the electrode 10 shown in FIG. 2, a radiopaque element 25 is also embodied as a thin annular ring or thin disc 25a and is preferably located concentric with and adjacent the contact 11 at the distal end 27 of the electrode 10 or adjacent all contacts 11. The electrode 10 may also include a length of radiopaque sheathing 25b at its proximal end 23.

The aforementioned radiopaque markers or elements 25 and sheathing 25b will be clearly visible using x-ray diagnostic techniques. Given the location of such markers 25 and sheathing 25b, the treating physician can ascertain the location of the marked and other contacts 11 with a high degree of accuracy.

In the embodiment 10c of the electrode 10 shown in FIG. 3, the radiopaque element 25 is the dielectric tubular body 16a on which the contacts are mounted. Further details regarding the construction of electrodes 10 of the grid, strip and depth types and of the manner of constructing such electrodes 10 using radiopaque elements 25 is shown and described in U.S. Pat. No. 4,903,702 which is assigned to the same assignee as this invention and which is incorporated herein by reference.

It should also be appreciated that such diagnostic electrodes 10, whether of the depth, grid or strip type, can be used for stimulation purposes. That is, the treating physician will slightly stimulate a portion of brain tissue adjacent each of the several contacts 11, 11a of an electrode 10 for further diagnostic purposes. Stimulation is by sequentially applying a small electrical current through each of several contacts 11, 11a to the adjacent brain tissue. Such current, usually no more than a few milliamperes, is permitted to flow and patient reaction is observed while stimulation is in process.

While researchers have conflicting opinions on this point, some are of the view that electrical contacts having significant iron content may, when stimulated, leave traces of iron deposited on brain tissue. Such iron deposits would clearly be undesirable. Since the electrical contacts 11, 11a of the inventive electrode 10 are preferably formed of a nickel-chromium alloy which is substantially devoid of iron (or at least has only very small traces of iron), such alloy minimizes the opportunity for depositions of iron upon brain tissue.

Once the foregoing is appreciated, the advantages of the new electrode 10 will be apparent. For example, the treating physician can employ newer types of diagnostic equipment, MRI equipment for example, and still be availed of an electrode 10 in which the location of contacts 11, 11a is readily apparent using such equipment. Additionally, the electrode 10 may optionally be made to also include radiopaque elements 25 so that the same electrode 10 may be used indiscriminately for MRI, CAT and/or x-ray diagnostic techniques. In either case, the physician is assured that any tendency of the contacts 11, 11a to deposit iron on brain tissue is minimized or eliminated when the new electrode 10 is used. Such significant advances in diagnostic electrode technology help improve the quality of patient treatment and care in the highly specialized field of neurosurgery. Such medical field, perhaps more than any other, requires accurate diagnosis and surgery.

While the principles of this invention have been described in connection with specific embodiments 10a, 10b, 10c it should be understood clearly that these descriptions are made only by way of example and are not intended to limit the scope of the invention.

What is claimed is:

1. An improved diagnostic electrode for intracranial implantation to determine the foci of diseased brain tissue and including:
    an electrode body;
    at least one metallic contact supported by the body;
    an electrical lead wire attached to the contact for connection to a diagnostic instrument;
    such metallic contact being made of an alloy which includes nickel and chromium and which is substantially devoid of iron;
the electrode thereby providing an essentially artifact-free image of the location of such metallic contact when contact location is determined using magnetic resonance imaging techniques.

2. The electrode of claim 1 wherein such body further includes a radiopaque element for locating such contact using x-ray diagnostic techniques.

3. The electrode of claim 2 adapted for use as a subdural strip electrode with plural radiopaque elements, at least one of which has a shape and location generally conforming to that of a metallic contact to indicate the position of such contact.

4. The electrode of claim 2 adapted for use as a subdural grid electrode with plural radiopaque elements, at least one of which has a shape and location generally conforming to that of a metallic contact to indicate the position of such contact.

5. The electrode of claim 2 adapted for use as a depth electrode having a body formed at least in part of a radiopaque material in contact with brain tissue when in use.

6. The electrode of claim 5 wherein substantially the entire body is made of such radiopaque material.

* * * * *